(12) United States Patent
Akagawa et al.

(10) Patent No.: US 10,591,407 B2
(45) Date of Patent: Mar. 17, 2020

(54) EXCREMENT ANALYSIS DEVICE, TOILET PROVIDED WITH SAID ANALYSIS DEVICE, AND METHOD FOR ANALYZING EXCREMENT

(71) Applicant: NEC Corporation, Tokyo (JP)

(72) Inventors: Takeshi Akagawa, Tokyo (JP); Masahiro Kubo, Tokyo (JP); Katsumi Abe, Tokyo (JP); Kimiyasu Takoh, Tokyo (JP); Ersin Altintas, Tokyo (JP); Yuji Ohno, Tokyo (JP); Tetsuri Ariyama, Tokyo (JP)

(73) Assignee: NEC Corporation, Tokyo (JP)

( * ) Notice: Subject to any disclaimer, the term of this patent is extended or adjusted under 35 U.S.C. 154(b) by 181 days.

(21) Appl. No.: 15/521,361

(22) PCT Filed: Oct. 23, 2015

(86) PCT No.: PCT/JP2015/005351
§ 371 (c)(1),
(2) Date: Apr. 24, 2017

(87) PCT Pub. No.: WO2016/063547
PCT Pub. Date: Apr. 28, 2016

(65) Prior Publication Data
US 2017/0307512 A1    Oct. 26, 2017

(30) Foreign Application Priority Data

Oct. 24, 2014    (JP) .................................. 2014-216906

(51) Int. Cl.
*G01N 21/01* (2006.01)
*A61B 10/00* (2006.01)
(Continued)

(52) U.S. Cl.
CPC ........... *G01N 21/01* (2013.01); *A61B 5/0075* (2013.01); *A61B 5/207* (2013.01); *A61B 5/6891* (2013.01);
(Continued)

(58) Field of Classification Search
CPC .... G01N 21/01; G01N 21/31; G01N 21/3563; G01N 21/3577; G01N 33/4833;
(Continued)

(56) References Cited

U.S. PATENT DOCUMENTS

2009/0309960 A1*  12/2009  Park .......................... G01J 3/02
                                                         348/61
2011/0051125 A1*   3/2011  Kim ....................... A61B 5/022
                                                         356/51
2013/0108236 A1    5/2013  Mestha et al.

FOREIGN PATENT DOCUMENTS

JP           5-5321          1/1993
JP        2007-252805       10/2007
(Continued)

OTHER PUBLICATIONS

International Search Report and Written Opinion dated Dec. 22, 2015, in corresponding PCT International Application.

*Primary Examiner* — Benjamin R Whatley
(74) *Attorney, Agent, or Firm* — Finnegan, Henderson, Farabow, Garrett & Dunner, L.L.P.

(57) ABSTRACT

Provided is an excrement analysis device capable of analyzing urine and feces simultaneously without increasing a burden of maintenance.
The excrement analysis device 10 of the present invention includes: a light source 20 that emits an inspection light toward an inspection area in a toilet bowl; spectroscopic information acquisition means 30 that receives an inspection light emitted toward the inspection area and acquires spectroscopic information from the received inspection light; and
(Continued)

analysis means 40 that extracts a first space containing the largest amount of urine components and a second space containing the largest amount of fecal components from the acquired spectroscopic information, and outputs a result of analysis of urine and feces on the basis of spectroscopic information regarding the first space and the second space.

6 Claims, 10 Drawing Sheets

(51) Int. Cl.
*G01N 33/493* (2006.01)
*G01N 21/31* (2006.01)
*G01N 21/3563* (2014.01)
*G01N 21/3577* (2014.01)
*G01N 33/483* (2006.01)
*A61B 5/00* (2006.01)
*A61B 5/20* (2006.01)
*G01N 21/78* (2006.01)

(52) U.S. Cl.
CPC ........ *A61B 10/007* (2013.01); *A61B 10/0038* (2013.01); *G01N 21/31* (2013.01); *G01N 21/3563* (2013.01); *G01N 21/3577* (2013.01); *G01N 33/4833* (2013.01); *G01N 33/493* (2013.01); *G01N 21/78* (2013.01)

(58) Field of Classification Search
CPC .... G01N 33/493; G01N 21/78; A61B 5/0075; A61B 5/207; A61B 5/6891; A61B 10/0038; A61B 10/007
See application file for complete search history.

(56) References Cited

FOREIGN PATENT DOCUMENTS

| | | | |
|---|---|---|---|
| JP | 2007252805 A | * 10/2007 | |
| JP | 2008-546430 | 12/2008 | |
| JP | 2009-204598 | 9/2009 | |
| JP | 2013-90922 | 5/2013 | |
| WO | WO-2006130847 A2 | * 12/2006 | ........... A61B 5/0066 |

* cited by examiner

EXCREMENT ANALYSIS DEVICE, TOILET PROVIDED WITH SAID ANALYSIS DEVICE, AND METHOD FOR ANALYZING EXCREMENT

CROSS-REFERENCE TO RELATED PATENT APPLICATIONS

This application is a National Stage Entry of International Application No. PCT/JP2015/005351, filed Oct. 23, 2015, which claims priority from Japanese Patent Application No. 2014-216906, filed Oct. 24, 2014. The entire contents of the above-referenced applications are expressly incorporated herein by reference.

TECHNICAL FIELD

The present invention relates to an excrement analysis device, a toilet provided with the analysis device, and a method for analyzing excrement, and more particularly, an excrement analysis device capable of analyzing urine and feces simultaneously, a toilet provided with the analysis device, and a method for analyzing excrement.

BACKGROUND ART

Various techniques for analyzing discharged urine by using an analysis device disposed on a toilet seat have been proposed. For example, an analysis device for measuring a glucose or bilirubin in urine by taking a portion of discharged urine in a predetermined portion of a toilet and by dipping a test paper or the like into the urine is known. Another known analysis device adds a precipitant to urine taken from a toilet bowl, and quantifies protein in the urine on the basis of the mass of the precipitate. Still another known analysis device introduces urine from a toilet bowl into a urine container, and measures a sugar or uric acid level in the urine through enzyme reactions. However, in all analysis devices, consumables, such as reagents or test papers, for measuring urine components and cleaning or the like of the urine collection mechanism are needed, and accordingly a heavy burden of maintenance is imposed.

PTL 1 discloses an analysis device that acquires components included in urine by using ATR-IR (Attenuated Total Reflectance Infrared Spectroscopy) to analyze a light reflected from the urine that has flowed into a urine collecting unit. The analysis device described in PTL 1 eliminates the need for consumables, such as reagents or test papers, as well as the need for cleaning the urine collecting unit.

Meanwhile, the recent growing health consciousness has created demand for the ability of analysis of both urine and feces simultaneously using an analysis device disposed on a toilet seat. For example, PTL 2 proposes disposing on a toilet seat an ultra-weak light instrument unit that measures a biogenic ultra-weak light emitted from urine and/or feces to measure such ultra-weak light when urine and/or feces are discharged.

CITATION LIST

Patent Literature

[PTL 1] Japanese Unexamined Patent Application Publication No. 2009-204598
[PTL 2] Japanese Unexamined Patent Application Publication No. 5-5321

SUMMARY OF INVENTION

Technical Problem

The analysis device described in PTL 1, however, is not capable of analyzing urine and feces simultaneously. PTL 2 proposes performing measurement of an ultra-weak light when urine and/or feces are discharged, but does not disclose any specific method for the measurement.

The present invention has been created in view of the problems described above, and an object of the invention is to provide an excrement analysis device that is capable of analyzing urine and feces simultaneously without increasing a burden of maintenance, a toilet equipped with such analysis device, and a method for analyzing excrement.

Solution to Problem

To achieve the above-described object, an excrement analysis device according to the present invention includes: a light source that emits an inspection light toward an inspection area in a toilet bowl; spectroscopic information acquisition means that receives an inspection light emitted toward the inspection area, acquires spectroscopic information from the received inspection light, and outputs the spectroscopic information; and analysis means that extracts a first space containing the largest amount of urine components and a second space containing the largest amount of fecal components from the spectroscopic information that has been output, and outputs a result of analysis of urine and feces on the basis of spectroscopic information regarding the extracted first and second spaces.

To achieve the above-described object, a toilet according to the present invention includes: a bowl into which urine and feces are discharged; and the above-described excrement analysis device, wherein the light source emits an inspection light toward an inspection area in the bowl.

To achieve the above-described object, a method for analyzing excrement of the present invention includes: receiving an inspection light emitted toward an inspection area in a toilet bowl, acquiring spectroscopic information from the received inspection light, and outputting the spectroscopic information; extracting a first space containing the largest amount of urine components and a second space containing the largest amount of fecal components from the spectroscopic information that has been output; and outputting a result of analysis of urine and feces on the basis of spectroscopic information regarding the extracted first and second spaces.

Advantageous Effects of Invention

According to the above-described aspects of the present invention, it is possible to provide an excrement analysis device capable of analyzing urine and feces simultaneously without increasing a burden of maintenance, a toilet equipped with such analysis device, and a method for analyzing excrement.

DESCRIPTION OF EMBODIMENTS

First Exemplary Embodiment

Figure 1:
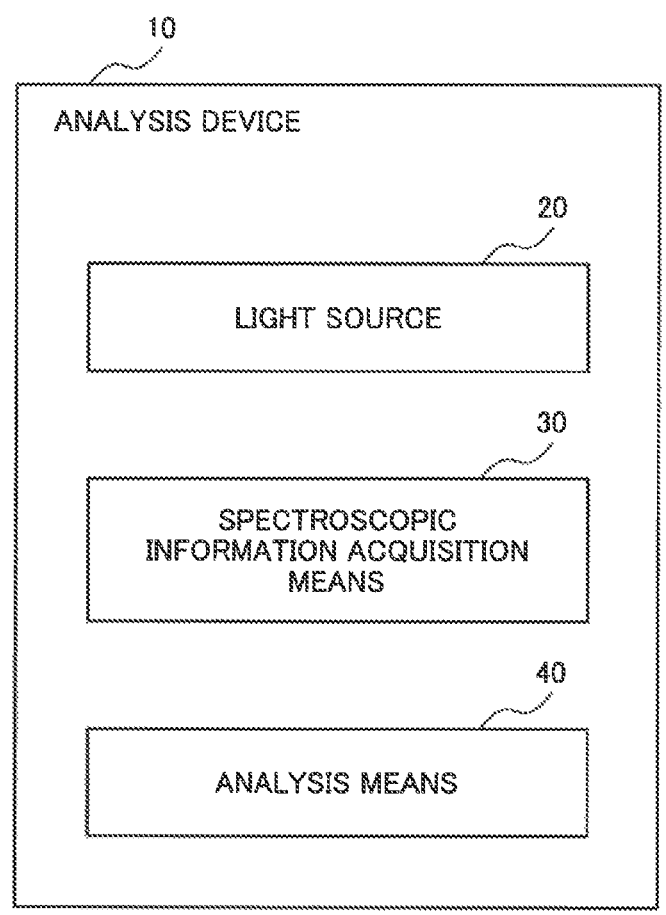
FIG. 1 is a block configuration diagram illustrating an excrement analysis device 10 according to a first exemplary embodiment.

A first exemplary embodiment of the present invention will now be described. FIG. 1 is a block configuration diagram illustrating an excrement analysis device according to the present exemplary embodiment. With reference to FIG. 1, the excrement analysis device 10 includes a light source 20, a spectroscopic information acquisition means 30, and an analysis means 40.

The light source 20 emits an inspection light toward a predetermined inspection area in a toilet bowl. The light source 20 according to the present exemplary embodiment emits an inspection light toward a predetermined inspection area when a mixture of water, urine, feces, and the like (hereinafter referred to as a sample) is held in a toilet bowl after a user discharges urine and/or feces into the bowl. The inspection light emitted by the light source 20 may be, for example, white light, broadband infrared light, or monochromatic light such as laser light.

The spectroscopic information acquisition means 30 acquires two-dimensional spectroscopic information regarding a sample, by receiving the inspection light that has been output by the light source 20 and has been transmitted or reflected by the sample in the inspection area and by analyzing the received inspection light. The spectroscopic information acquisition means 30 also acquires three-dimensional spectroscopic information regarding a sample, by moving the focal position in the optical axis direction of the inspection light or due to the sample being moved in the optical axis direction of the inspection light. Methods for moving a sample in the optical axis direction may include, for example, a method for disposing a drive mechanism, or a method for generating a small wave in the light axis direction in the bowl by emitting a weak ultrasound wave toward the vicinity of the inspection area.

The spectroscopic information acquisition means 30 outputs the acquired two-dimensional or three-dimensional spectroscopic information to the analysis means 40 using wired or wireless communication. As the spectroscopic information acquisition means 30, a hyperspectral camera capable of simultaneously acquiring spatial information and spectral information may be used, for example. As the spectroscopic information acquisition means 30, a spectroscope may also be used. In the case where a hyperspectral camera is used, three-dimensional spectroscopic information is acquired by moving the hyperspectral camera or the sample in the optical axis direction of an inspection light to move the focal position.

The spectroscopic information acquisition means 30 is preferably placed near the inspection area. However, when the spectroscopic information acquisition means 30 may not be placed near the inspection area due to, for example, constraints of size of the spectroscopic information acquisition means 30, the inspection light transmitted or reflected by a sample in the inspection area can be led to the spectroscopic information acquisition means 30 through, for example, an optical fiber placed between the inspection area and the spectroscopic information acquisition means 30.

The analysis means 40 extracts a first space containing the largest amount of urine components and a second space containing the largest amount of fecal components from the inspection area, through an image analysis performed on the two-dimensional or three-dimensional spectroscopic information that has been input from the spectroscopic information acquisition means 30. In addition, the analysis means 40 acquires, from the spectroscopic information, spectral information regarding the extracted first and second spaces, analyzes components contained in the first and second spaces on the basis of peak values in the acquired spectral information, and then outputs results of analysis of urine and feces. For example, the analysis means 40 extracts wavelengths corresponding to peaks exhibited in the acquired spectral information, determines the type of component, such as sugar, protein, uric acid, sodium, potassium, stress hormone, or blood, from the extracted wavelengths, identifies the amount of the identified component on the basis of intensity values of the peaks, and outputs the result as a result of analysis of urine and feces.

If an image analysis on spectroscopic information fails to extract a first space and a second space due to some problem such as an improper condition of the sample or inferior quality of the spectroscopic information, first and second spaces may be determined by setting some candidate spaces, analyzing the spectral information regarding each candidate space, and determining a first space containing the largest amount of urine components and a second space containing the largest amount of fecal components on the basis of the result of analysis on some pieces of spectral information.

In the excrement analysis device 10 configured as above, the analysis means 40 extracts a first space containing the largest amount of urine components and a second space containing the largest amount of fecal components, through an image analysis performed on the two-dimensional or three-dimensional spectroscopic information that has been input from the spectroscopic information acquisition means 30. Then, the analysis means 40 acquires spectral information regarding the extracted first and second spaces, and outputs results of analysis of urine and feces on the basis of the spectral information. In this case, high-precision analysis of each of components contained in urine and feces can be achieved with an inspection light emitted for a short time.

In addition, in the excrement analysis device 10 configured as above, the light source 20 is used to emit an inspection light toward the inspection area in the toilet bowl, and the spectroscopic information acquisition means 30 acquires two-dimensional or three-dimensional spectroscopic information from the inspection light that has been transmitted through, or reflected from, the inspection area. In this case, long-term acquisition of spectroscopic information about samples can be achieved almost without maintenance as to replenishing consumables such as reagents and test papers.

Therefore, the excrement analysis device 10 according to the present exemplary embodiment achieves simultaneous analysis of urine and feces without increasing a burden of maintenance.

Second Exemplary Embodiment

Figure 2:
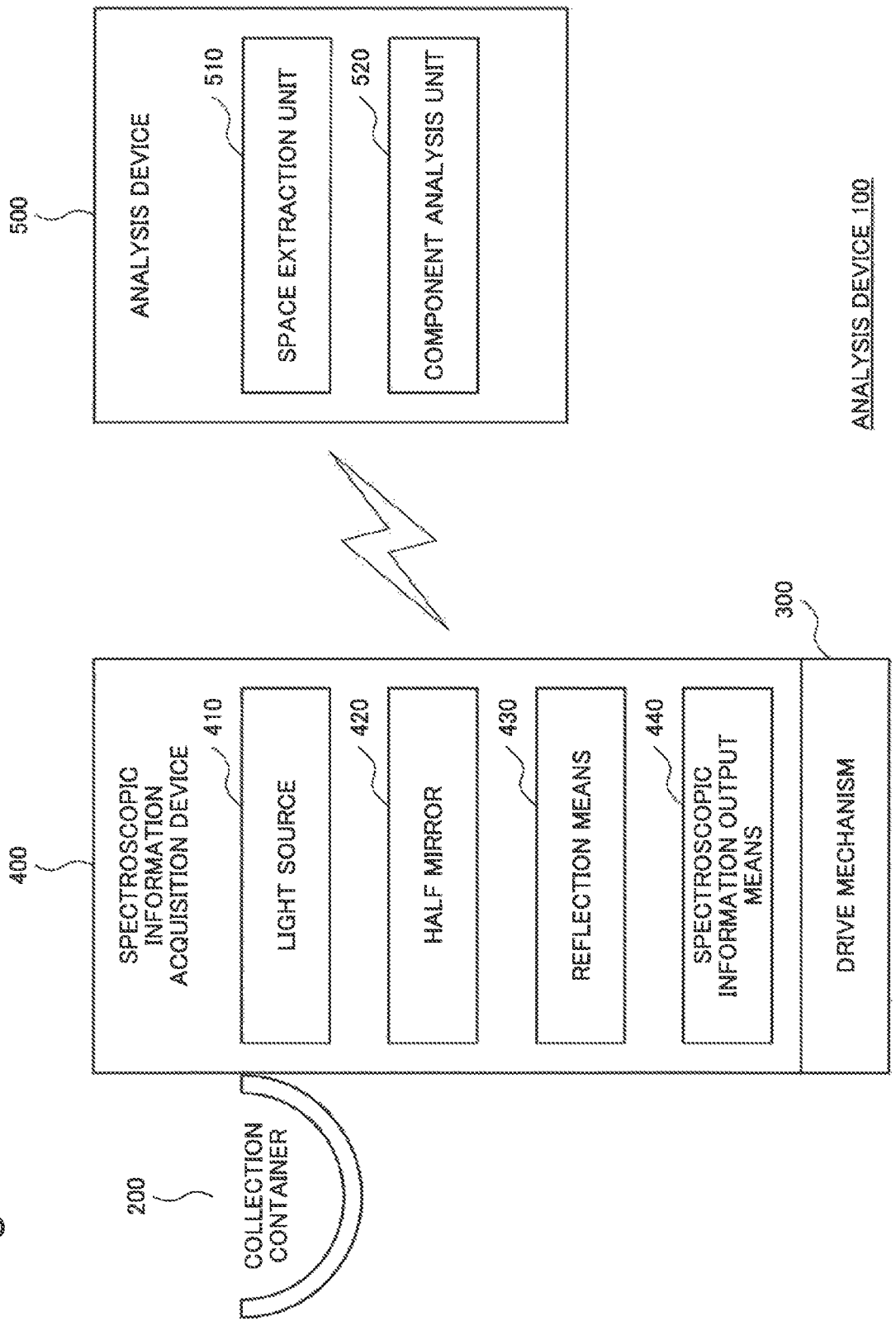
FIG. 2 is a block configuration diagram illustrating an excrement analysis device 100 according to a second exemplary embodiment.

A second exemplary embodiment will now be described. FIG. 2 is a block configuration diagram illustrating an excrement analysis device according to the present exemplary embodiment. With reference to FIG. 2, the excrement analysis device 100 includes a collection container 200, a drive mechanism 300, a spectroscopic information acquisition device 400, and an analysis device 500. The collection container 200, the drive mechanism 300, and the spectroscopic information acquisition device 400 are embedded in a toilet bowl, which is not illustrated in FIG. 2.

Figure 3:
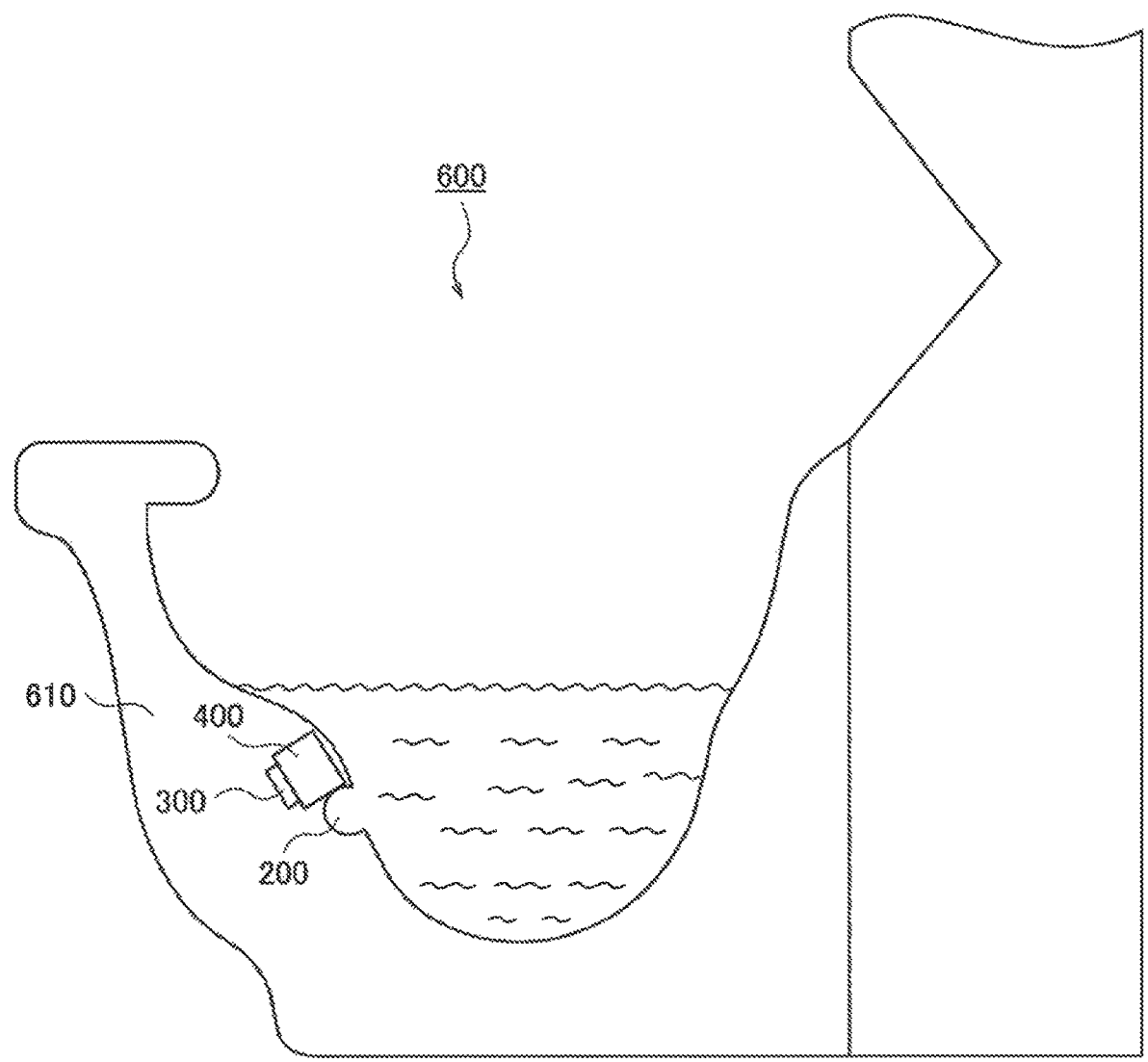
FIG. 3 is a cross-sectional view of a toilet 600 having a bowl 610 in which a collection container 200, a drive mechanism 300, and a spectroscopic information acquisition device 400 of the excrement analysis device 100 according to the second exemplary embodiment are embedded.

FIG. 3 is an exemplary cross-sectional view of a toilet having a bowl in which the collection container 200, the drive mechanism 300, and the spectroscopic information acquisition device 400 are embedded. With reference to FIG. 3, the collection container 200, the drive mechanism 300, and the spectroscopic information acquisition device 400 are embedded inside the front of the bowl 610 of the toilet 600 such that the drive mechanism 300 and the spectroscopic information acquisition device 400 are placed near the collection container 200.

Note that the collection container 200, the drive mechanism 300, and the spectroscopic information acquisition device 400 may also be embedded inside the bottom or inside the back of the bowl 610. Alternatively, with the bowl 610 itself being used as a large collection container, the drive mechanism 300 and the spectroscopic information acquisition device 400 may be placed inside or around the bowl 610. Still alternatively, if the drive mechanism 300 and the spectroscopic information acquisition device 400 may not be placed near the collection container 200 due to constrains and the like of size, an optical fiber, for example, may be disposed between a half mirror 420 (described later) and the collection container 200 to transmit an inspection light, a reference light, and a light under inspection via the optical fiber.

The following describes the individual elements of the excrement analysis device 100.

The collection container 200, which is made of a transparent member, has an open top and is embedded inside the bowl 610 below the water surface in such a way that the container's open surface is continuous with the inner surface of the bowl 610 of the toilet 600, as illustrated in FIG. 3. As a result, the collection container 200 will be filled with substances gathering in the bowl 610 of the toilet 600. For example, inside of the collection container 200 is usually filled with water. When the user discharges urine and/or feces into the bowl 610 of the toilet 600, at inside of the collection container 200, a mixture of water, urine, feces, and the like (hereinafter referred to as a sample) is filled.

The drive mechanism 300 causes the spectroscopic information acquisition device 400 to move, according to the inspection area, in a plane orthogonal to the optical axis direction (hereinafter referred to as in the inspection plane) of an inspection light emitted toward the inspection area. Due to the drive mechanism 300 causing the spectroscopic information acquisition device 400 to move in the inspection plane, a three-dimensional tomographic image and its corresponding spectral information regarding a sample filled into the collection container 200 are acquired. Instead of the spectroscopic information acquisition device 400 being move by the drive mechanism 300, the collection container 200 or a sample in the collection container 200 may be moved in the inspection plane.

Figure 4:
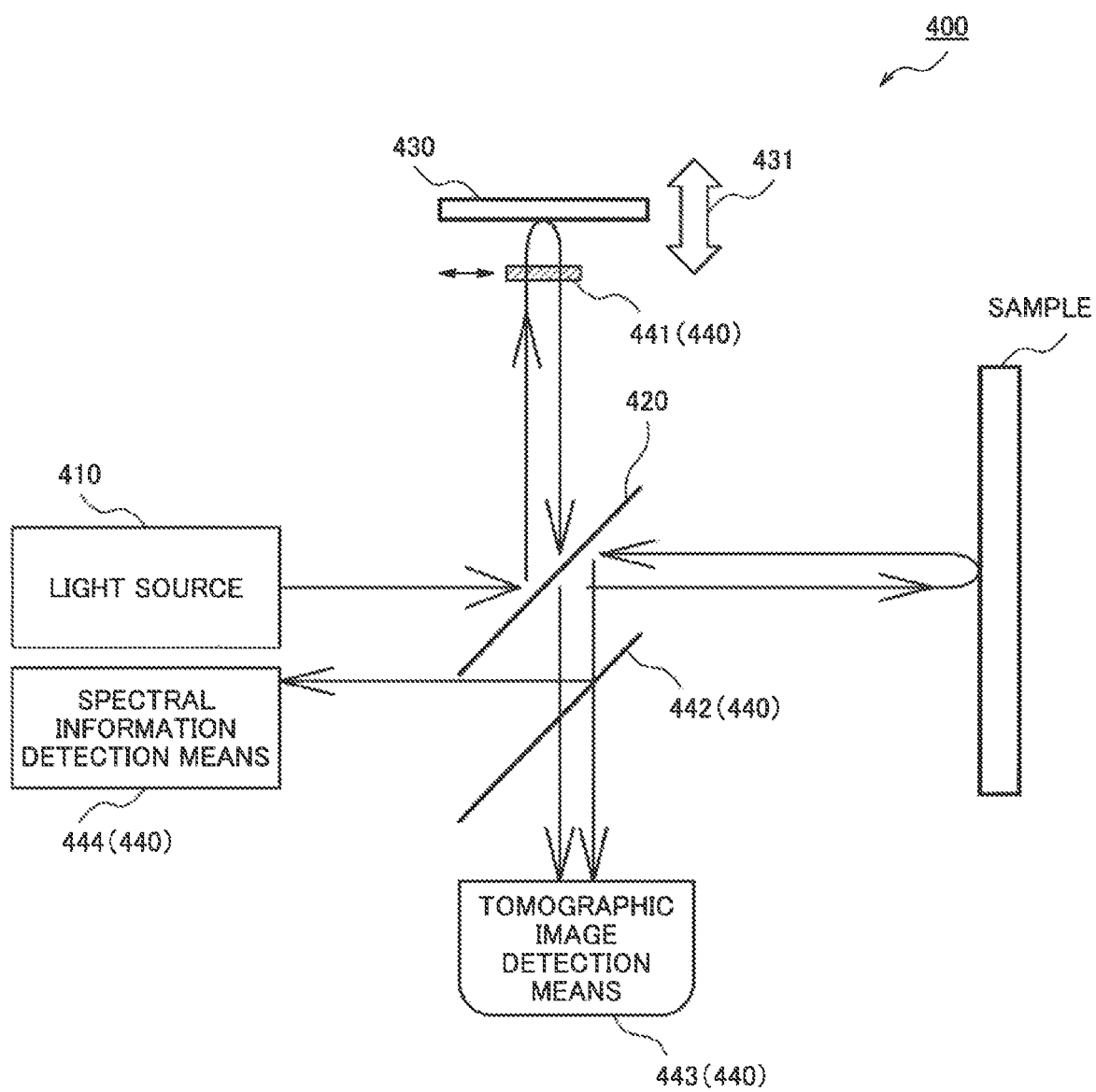
FIG. 4 is a configuration diagram illustrating the spectroscopic information acquisition device 400 according to the second exemplary embodiment.

The spectroscopic information acquisition device 400 is placed near the collection container 200 and is moved in the inspection plane by the drive mechanism 300. With a state positional control being applied by the drive mechanism 300, the spectroscopic information acquisition device 400 emits an inspection light onto a sample in the collection container 200, receives the inspection light reflected by the sample, and acquires three-dimensional spectroscopic information based on the received inspection light to output the information to the analysis device 500. The spectroscopic information acquisition device 400 according to the present exemplary embodiment sends the acquired three-dimensional spectroscopic information to the analysis device 500 using wireless communication. As the spectroscopic information acquisition device 400, OCT (optical coherence tomography), for example, may be used. FIG. 4 is a configuration diagram illustrating such spectroscopic information acquisition device 400. As illustrated in FIGS. 2 and 4, the spectroscopic information acquisition device 400 includes a light source 410, a half mirror 420, a reflection means 430, and a spectroscopic information output means 440.

The light source 410 emits an inspection light toward the half mirror 420. The inspection light emitted by the light source 410 may be, for example, broadband infrared light.

The half mirror 420 splits the inspection light input from the light source 410 into two inspection lights, outputs one inspection light to the reflection means 430, and outputs the other inspection light to the inspection area that includes a sample in the collection container 200. Then, the half mirror 420 guides both the inspection light reflected by the reflection means 430 (hereinafter referred to as a reference light) and the inspection light reflected by the sample located in the inspection area in the collection container 200 (hereinafter referred to as a light under inspection) into the spectroscopic information output means 440.

The reflection means 430 causes the inspection light incoming from the half mirror 420 to be reflected toward a side of the half mirror 420 (a reference light). The reflection means 430 according to the present exemplary embodiment includes an optical path length adjustment means 431 for the purpose of moving the reflection means 430. As the optical path length adjustment means 431 moves the reflection means 430 in the optical axis direction of a reference light, the phase of the reference light is changed.

The spectroscopic information output means 440, which includes a shutter 441, a beam splitter 442, a tomographic image detection means 443, and a spectral information detection means 444 as illustrated in FIG. 4, acquires three-dimensional spectroscopic information from the inspection light (light under inspection) reflected by a sample contained in the collection container 200.

The shutter 441, which is placed between the reflection means 430 and the half mirror 420, blocks at predetermined intervals the reference light entering the half mirror 420 from the reflection means 430.

The beam splitter 442 distributes incoming lights from the half mirror 420 to the tomographic image detection means 443 and to the spectral information detection means 444.

The tomographic image detection means 443 detects, in synchronization with the driving intervals for the shutter 441, interference lights between the reference light and the light under inspection entering from the beam splitter 442, and acquires their interference signals. Specifically, while the reference light is not blocked by the shutter 441, the tomographic image detection means 443 detects an interference light between the reference light and the light under inspection entering from the half mirror 420. Due to the optical path length adjustment means 431 causing the reflection means 430 to move in the optical axis direction of the reference light, the tomographic image detection means 443 detects an interference signal that depends on the optical path length difference, and acquires a reflected light intensity distribution. In addition, due to the drive mechanism 300 causing the spectroscopic information acquisition device 400 to move in the inspection plane, the tomographic image detection means 443 acquires an interference signal on the inspection plane. Then, on the basis of a reflected light intensity distribution of a plurality of interference signals along the optical axis direction and in the inspection plane, the tomographic image detection means 443 acquires a three-dimensional tomographic image of a sample filled into the collection container 200.

The spectral information detection means 444 acquires, in synchronization with the driving intervals for the shutter 441, spectral information regarding the light under inspection entering from the beam splitter 442. Specifically, while the reference light is blocked by the shutter 441, the spectral information detection means 444 acquires spectral information regarding the light under inspection entering from the half mirror 420.

The spectroscopic information output means 440 sends the three-dimensional tomographic image acquired by the tomographic image detection means 443 and the spectral information acquired by the spectral information detection means 444, which are collectively three-dimensional spectroscopic information, to the analysis device 500.

The analysis device 500, which includes a space extraction unit 510 and a component analysis unit 520 as illustrated in FIG. 2, is placed at a position visible or otherwise sensible from the user. The analysis device 500 analyzes the three-dimensional spectroscopic information received from the spectroscopic information acquisition device 400, and then outputs the user's health information.

Figure 5:
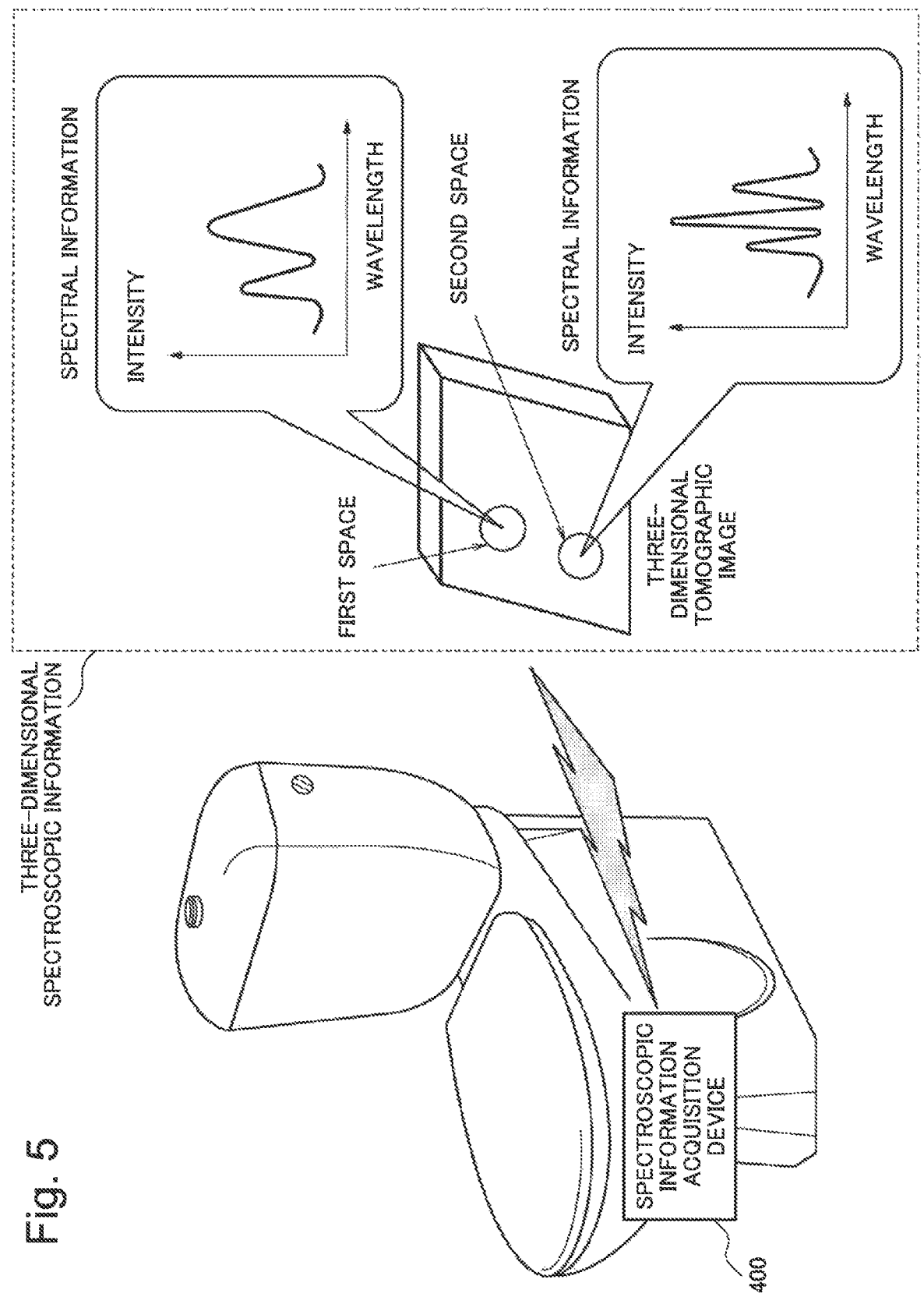
FIG. 5 is a conceptual diagram showing that the excrement analysis device 100 of the second exemplary embodiment acquires spectral information pieces regarding a first space and a second space from a three-dimensional tomographic image.

The space extraction unit 510 extracts a first space containing the largest amount of urine components and a second space containing the largest amount of fecal components, by performing image processing on the three-dimensional tomographic image, which is part of the three-dimensional spectroscopic information received from the spectroscopic information acquisition device 400. The space extraction unit 510 extracts from the three-dimensional spectroscopic information the spectral information pieces corresponding to the extracted first space and second space, and outputs the spectral information pieces to the component analysis unit 520. FIG. 5 is a conceptual diagram showing that a first space and a second space are determined on the basis of a three-dimensional tomographic image, and that spectral information pieces regarding samples located at the determined first and second spaces are acquired.

The component analysis unit 520 includes a storage unit that stores the user's health information. The component analysis unit 520 determines whether a specific component is included in the urine or feces by analyzing the incoming spectral information pieces corresponding to the first and second spaces and, if the specific component is included, the component analysis unit 520 identifies the amount of the component contained in the urine or feces. Particularly, the component analysis unit 520 extracts wavelengths of peaks exhibited in the acquired spectral information, identifies the type of component from the extracted wavelengths, and identifies the amount of the identified component from intensity values of the peaks. Examples of identified components may include sugar, protein, uric acid, sodium, potassium, stress hormone, and blood.

Figure 6:
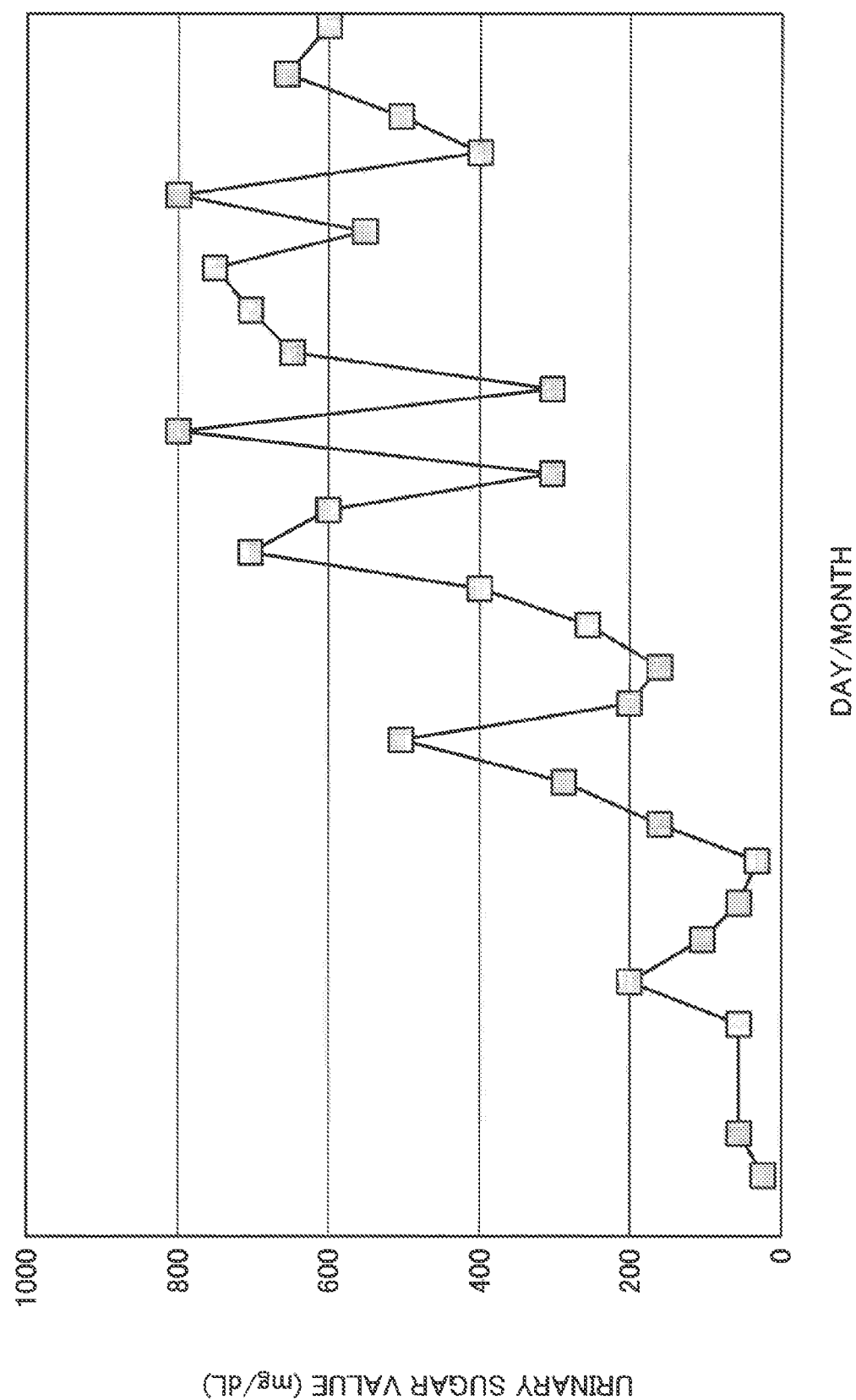
FIG. 6 illustrates an example of a user's health information displayed by the analysis device 500 according to the second exemplary embodiment.

The component analysis unit 520 updates the user's health information by adding a result of analysis on the newly acquired spectral information to the user's health information stored in the storage unit, and outputs the updated user's health information to a display unit or the like (not illustrated). FIG. 6 illustrates an example of the user's health information displayed on the display unit. FIG. 6 shows change in the amount of sugar contained in the user's urine (urinary sugar values) over time. When the urinary sugar value exceeds a predetermined threshold, the component analysis unit 520 may, for example, display an additional alarm or automatically transfer the user's health information to an external server or a medical institution. Instead of displaying change in urinary sugar values over time, a trend in relative value, for example, may be displayed as the user's health information, the relative value being calculated by dividing the identified urinary sugar value by a separately provided urinary sugar value (a reference value).

Figure 7:
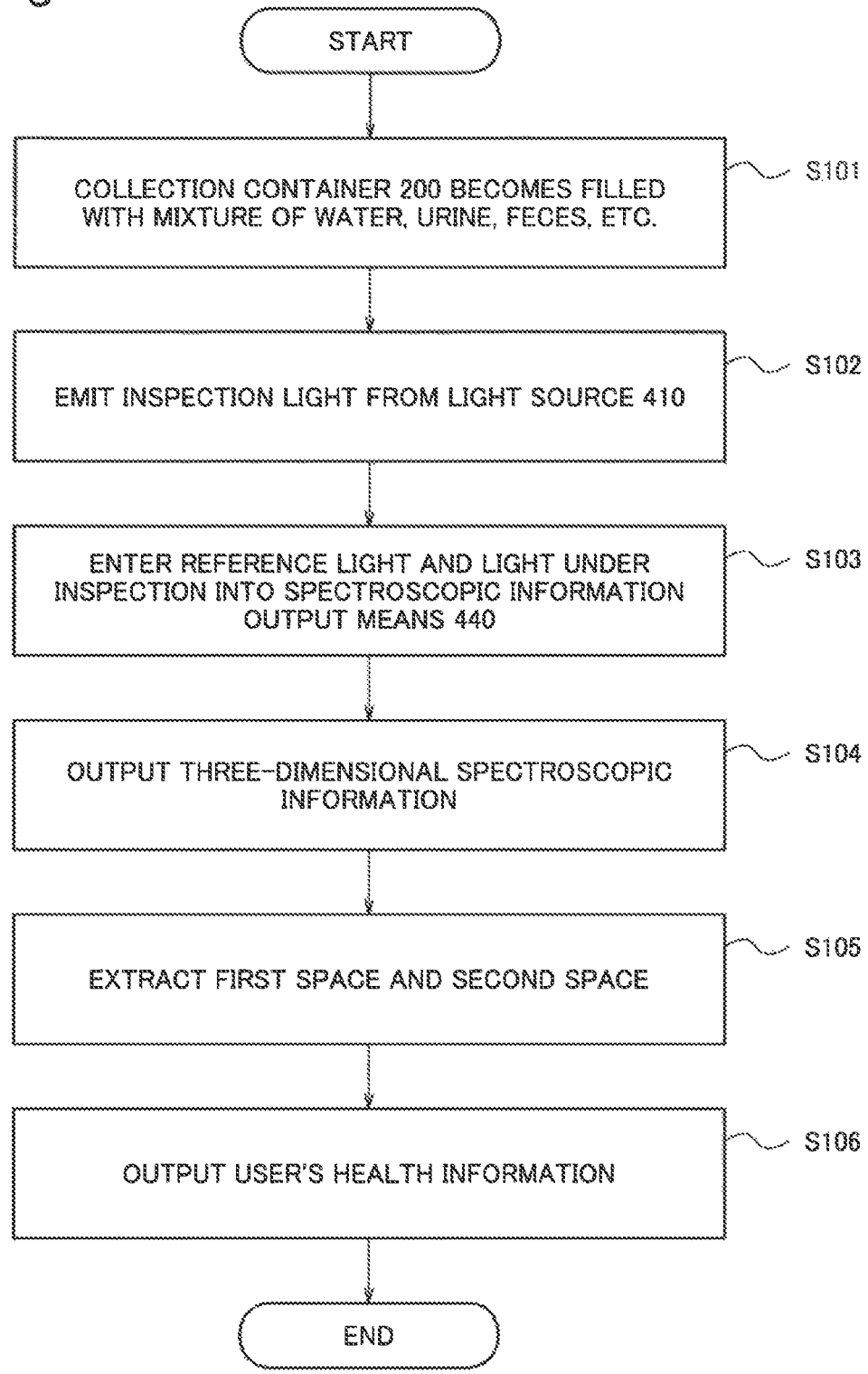
FIG. 7 is an operation flow diagram for the excrement analysis device 100 according to the second exemplary embodiment.

Operation processes for the excrement analysis device 100, which is configured as above, will now be described by following steps in FIG. 7. The collection container 200 in the initial state is filled with water. Inside of the collection container 200 becomes filled with a mixture of water, urine, feces, and the like (a sample) when the user discharges urine and/or feces into the bowl 610 of the toilet 600 (S101).

When the inside of the collection container 200 is filled with a mixture of water, urine, feces, and the like, the drive mechanism 300, the spectroscopic information acquisition device 400, and the analysis device 500 are activated. Alternatively, the drive mechanism 300, the spectroscopic information acquisition device 400, and the analysis device 500 may be activated by, for example, the user pressing a predetermined button, or may be automatically activated when the discharge of the urine or feces are detected by a weight sensor or a water level detection sensor.

The spectroscopic information acquisition device 400, with a state of being moved in the inspection plane by the drive mechanism 300, emits an inspection light from the light source 410 (S102). The inspection light emitted from the light source 410 is split at the half mirror 420 into two inspection lights, and then one inspection light is output to the reflection means 430, while the other inspection light is output to a predetermined inspection area in the collection container 200. Then, the inspection light reflected by the reflection means 430, which is now a reference light, is incoming to the half mirror 420 again, while the inspection light reflected at the mixture of water, urine, feces, and the like located within the inspection area in the collection container 200, which is now a light under inspection, is incoming to the half mirror 420 again. The half mirror 420 guides the incoming reference light and light under inspection into the spectroscopic information output means 440 (S103).

The spectroscopic information output means 440 acquires a three-dimensional tomographic image at the tomographic image detection means 443, as well as acquiring spectral information at the spectral information detection means 444, and then sends such image and information, which are collectively three-dimensional spectroscopic information, to the analysis device 500 (S104).

In the analysis device 500, the space extraction unit 510 extracts a first space containing the largest amount of urine components and a second space containing the largest amount of fecal components by performing an image analysis on the three-dimensional spectroscopic information that has been input, and outputs spectral information pieces regarding mixtures loaded into the extracted first space and second space to the component analysis unit 520 (S105). The component analysis unit 520 analyzes components included in urine and feces, on the basis of the spectral information pieces that have been input, and outputs analysis results as the user's health information (S106).

As seen above, in the excrement analysis device 100 according to the present exemplary embodiment, the analysis device 500 extracts a first space containing the largest amount of urine components and a second space containing the largest amount of fecal components by performing an image analysis on a three-dimensional tomographic image, and then analyzes components contained in urine and feces on the basis of spectral information pieces regarding the extracted first space and second space. In this case, high-precision analysis of each of components contained in urine and feces can be achieved with an inspection light emitted for a short time.

In addition, the excrement analysis device 100 according to the present exemplary embodiment, with the collection container 200 embedded in the inside of the bowl 610 below the water surface in the bowl 610 of the toilet 600, emits an inspection light from the light source 410 toward a mixture of urine, feces, and the like loaded into the collection container 200, receives the inspection light reflected by the mixture, and acquires three-dimensional spectroscopic information. In this case, long-term acquisition of three-dimensional spectroscopic information about excrement can be achieved almost without maintenance as to replenishing of consumables such as reagents and test papers.

Figure 8:
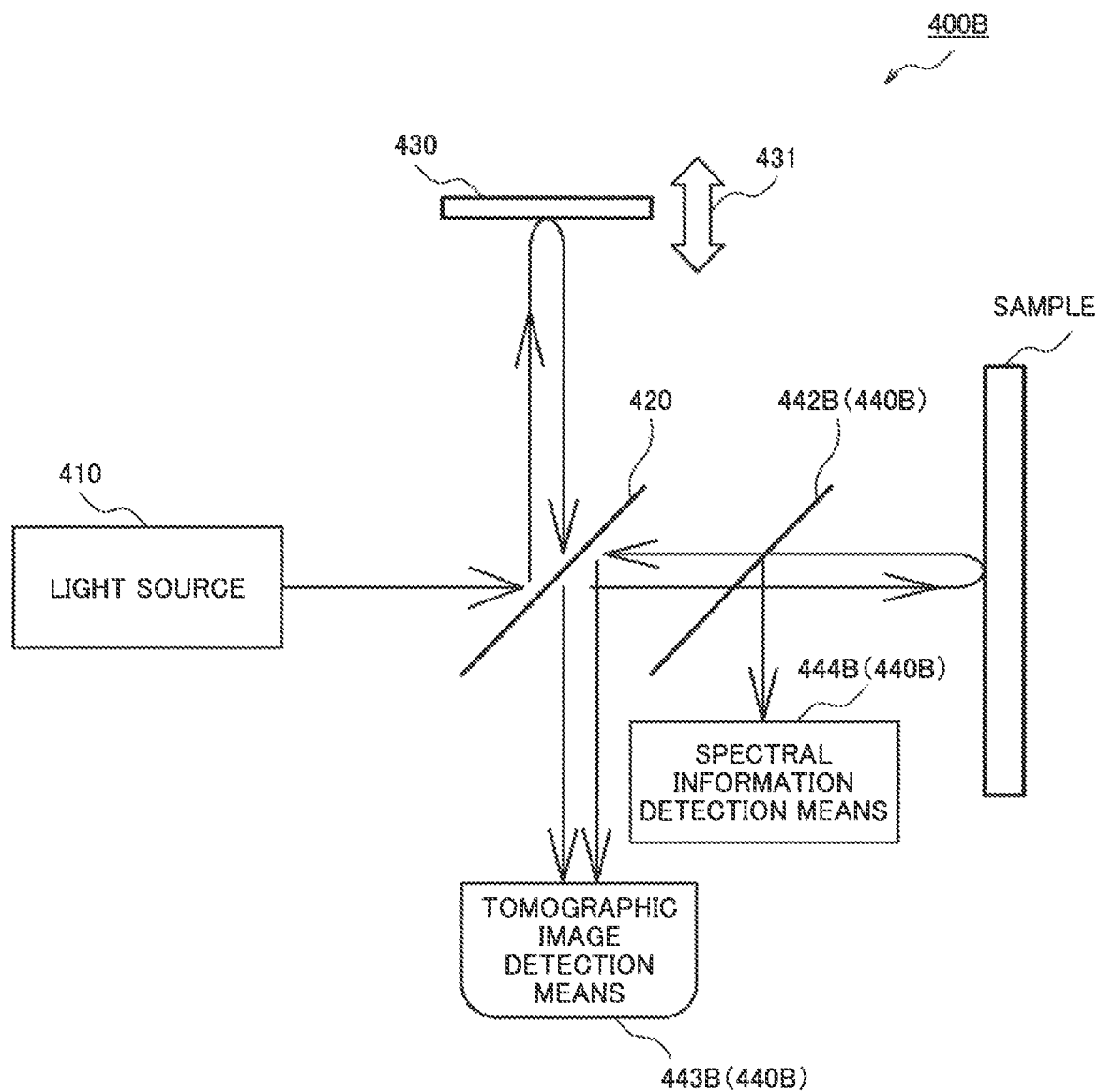
FIG. 8 is a configuration diagram illustrating another spectroscopic information acquisition device 400B according to the second exemplary embodiment.

Alternatively, in the spectroscopic information acquisition device 400, the beam splitter 442 and the spectral information detection means 444 may be placed between the sample and the half mirror 420. FIG. 8 is a configuration diagram illustrating such spectroscopic information acquisition device. In the spectroscopic information acquisition device 400B in FIG. 8, which has the beam splitter 442B and the spectral information detection means 444B placed between a sample and the half mirror 420, the beam splitter 442B directly causes part of the light under inspection reflected by the sample to diverge, and the light is then detected by the spectral information detection means 444B. Although creating some influences such as intensity decay and dispersion, this configuration eliminates the need for a shutter and, at the same time, achieves continuous acquisition of three-dimensional tomographic images and spectral information without synchronizing the tomographic image detection means 443B and the spectral information detection means 444B with a shutter.

Third Exemplary Embodiment

Figure 9:
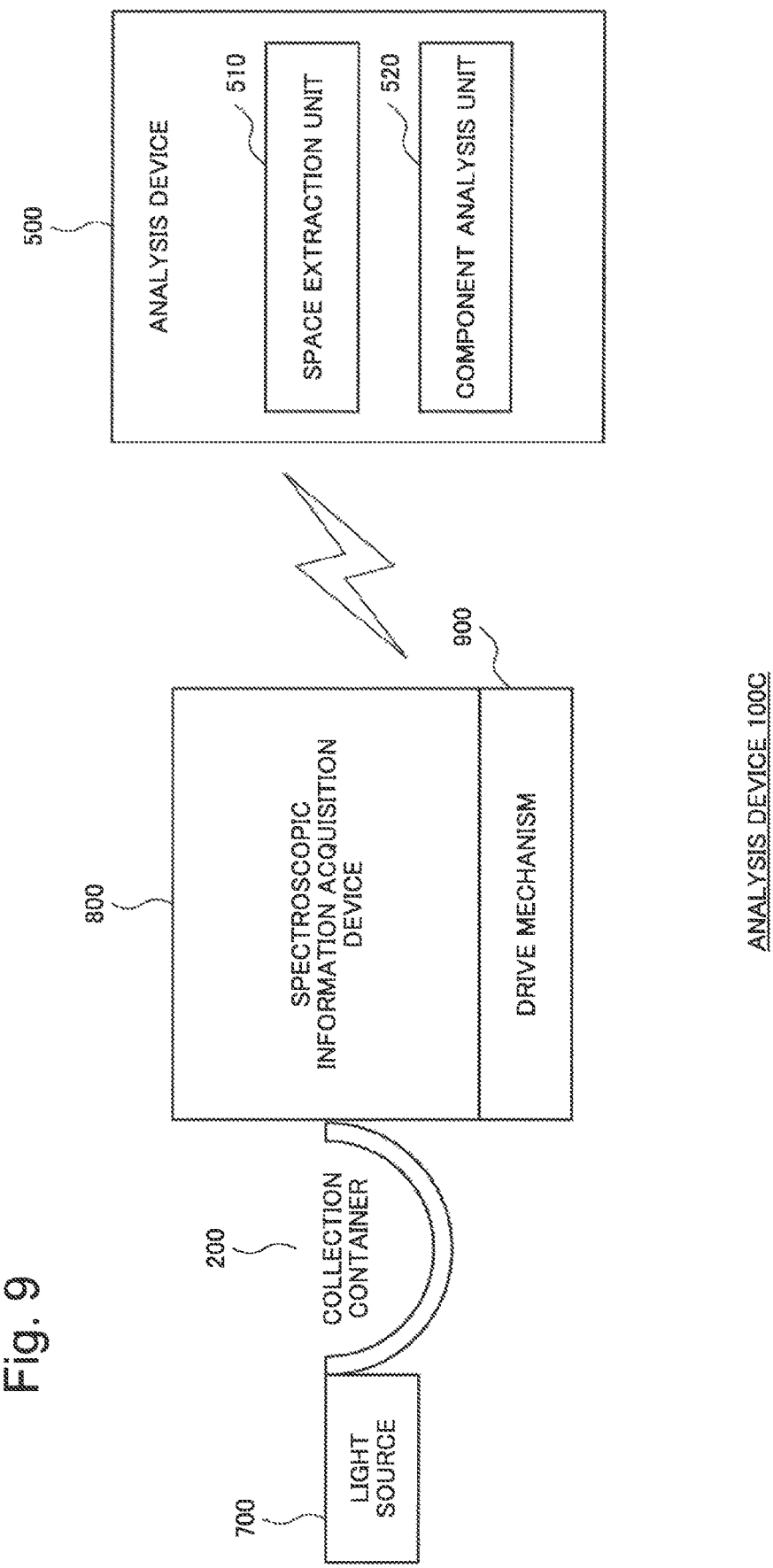
FIG. 9 is a block configuration diagram illustrating an excrement analysis device 100C according to a third exemplary embodiment.
Figure 10:
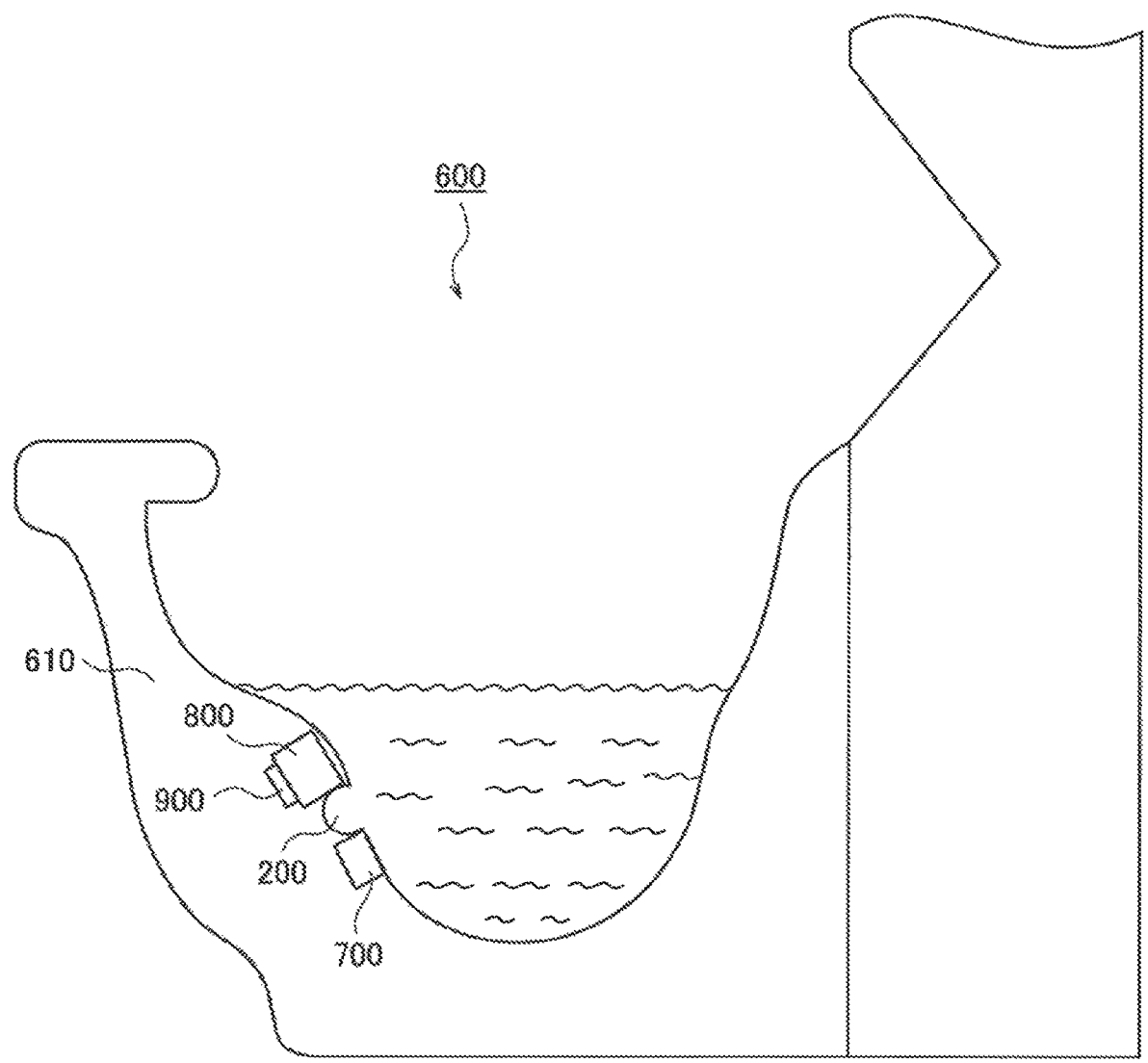
FIG. 10 is a cross-sectional view of a toilet 600 having a bowl 610 in which a collection container 200, a drive mechanism 300, a light source 700, a spectroscopic information acquisition device 800, and a drive mechanism 900 of the excrement analysis device 100C according to the third exemplary embodiment are embedded.

A third exemplary embodiment will now be described. The excrement analysis device 100C according to the present exemplary embodiment detects and analyzes an inspection light that has been transmitted through a sample (hereinafter referred to as a light under inspection). FIG. 9 is a block configuration diagram illustrating the excrement analysis device 100C. With reference to FIG. 9, the excrement analysis device 100C includes a collection container 200, a light source 700, a spectroscopic information acquisition device 800, a drive mechanism 900, and an analysis device 500. FIG. 10 is a cross-sectional view of a toilet having a bowl in which the collection container 200, the light source 700, the spectroscopic information acquisition device 800, and the drive mechanism 900 are embedded. As illustrated in FIG. 10, in the present exemplary embodiment, the collection container 200 is placed between the light source 700, and the spectroscopic information acquisition device 800 and the drive mechanism 900.

The light source 700 emits an inspection light toward a predetermined inspection area in the toilet bowl 610.

With a state that a position is controlled by the drive mechanism 900, the spectroscopic information acquisition device 800 receives the light under inspection that has been emitted by the light source 700 and has been transmitted through the sample, acquires three-dimensional spectroscopic information based on the received light under inspection, and outputs the information to the analysis device 500. A hyperspectral camera or a spectroscope, for example, may be used as the spectroscopic information acquisition device 800.

The drive mechanism 900 causes the spectroscopic information acquisition device 800 to move according to the inspection area. Due to the drive mechanism 900 causing the spectroscopic information acquisition device 800 to move in the inspection plane and in the optical axis direction of the inspection light, three-dimensional spectroscopic information regarding a sample loaded into the collection container 200 is acquired. Three-dimensional spectroscopic information regarding a sample can also be acquired by causing the light source 700 to move in the inspection plane and in the optical axis direction of the inspection light, instead of the spectroscopic information acquisition device 800 being moved by the drive mechanism 900. Furthermore, the collection container 200 or a sample in the collection container 200 may be caused to move in the inspection plane and in the optical axis direction of the inspection light.

The analysis device 500 analyzes the three-dimensional spectroscopic information received from the spectroscopic information acquisition device 800, and then outputs the user's health information. The analysis device 500 functions in a similar manner to the analysis device 500 in FIG. 2 as described in the second exemplary embodiment, and thus its detail description is omitted.

The excrement analysis device 100C as configured above also achieves high-precision analysis of components included in urine and feces with an inspection light emitted for a short time, by analyzing components contained in urine and feces on the basis of spectral information pieces regarding a first space and a second space extracted by the analysis device 500.

In addition, the excrement analysis device 100C according to the present exemplary embodiment, which has the collection container 200 embedded in the inside of the bowl 610 below the water surface in the bowl 610 of the toilet 600, emits an inspection light from the light source 700 toward a mixture of urine, feces, and the like loaded into the collection container 200, receives the light under inspection that has been transmitted through the mixture, and acquires three-dimensional spectroscopic information. In this case, long-term acquisition of three-dimensional spectroscopic information about excrement can be achieved almost without maintenance as to replenishing of consumables such as reagents and test papers.

Fourth Exemplary Embodiment

A fourth exemplary embodiment will now be described. The excrement analysis device according to the present exemplary embodiment is configured in a similar manner to the excrement analysis device 100C described in the third exemplary embodiment with reference to FIGS. 9 and 10. The light source 700 according to the present exemplary embodiment emits laser light as the inspection light. In this case, the light source 700 emits laser light onto the sample in the collection container 200, and then the inspection light scattered in the sample (Raman scattering light) is analyzed by the analysis device 500. That is, on the basis of the Raman spectrum acquired by the spectroscopic information acquisition device 800, the analysis device 500 determines, for example, whether any specific component is contained in urine or feces. Using a light source that emits laser light as the inspection light provides a longer optical path of the incident light in the sample, compared with the second and third exemplary embodiments which use a light source emitting broadband infrared light as the inspection light. A longer optical path in a sample can reduce the influence of relative changes in the amount of a collected sample, thereby improving reliability of measurement of component information.

The present invention is not limited to the above exemplary embodiments and includes design changes and the like that do not depart from the gist of the present invention. The part or whole of the above exemplary embodiments can be described as, but is not limited to, the following supplementary notes.

[Supplementary Note 1]

An excrement analysis device comprising:

a light source that emits an inspection light toward an inspection area in a toilet bowl;

spectroscopic information acquisition means that receives the inspection light emitted toward the inspection area, acquires spectroscopic information from the received inspection light, and outputs the spectroscopic information; and analysis means that extracts a first space containing the largest amount of urine components and a second space containing the largest amount of fecal components from the spectroscopic information that has been output, and outputs a result of analysis of urine and feces on the basis of the spectroscopic information regarding the extracted first space and second space.

[Supplementary Note 2]

The excrement analysis device according to supplementary note 1, wherein the spectroscopic information acquisition means receives an inspection light that has been transmitted through the inspection area.

[Supplementary Note 3]

The excrement analysis device according to supplementary note 2, wherein the spectroscopic information acquisition means is a hyperspectral camera, and further includes drive means that causes the hyperspectral camera to move in an optical axis direction of the inspection light, and the hyperspectral camera outputs three-dimensional spectroscopic information by moving in the optical axis direction.

[Supplementary Note 4]

The excrement analysis device according to supplementary note 2 or 3, further including optical transmission means that leads an inspection light emitted toward the inspection area to the hyperspectral camera.

[Supplementary Note 5]

The excrement analysis device according to any one of supplementary notes 1 to 4, wherein the spectroscopic information acquisition means receives an inspection light that has been emitted by the light source and has been transmitted through the inspection area.

[Supplementary Note 6]

The excrement analysis device according to supplementary note 1, wherein the spectroscopic information acquisition means receives an inspection light that has been reflected from the inspection area.

[Supplementary Note 7]

The excrement analysis device according to supplementary note 6, wherein the light source and the spectroscopic information acquisition means are composed of OCT, and further include drive means that causes the OCT to move such that the inspection light scans across an inspection area in the bowl, wherein the spectroscopic information acquisition means includes:

a half mirror that splits the emitted inspection light into two inspection lights, outputs one inspection light to reflection means while outputting the other inspection light to the inspection area, and outputs, as a reference light, the one inspection light reflected by the reflection means while outputting, as a light under inspection, the other inspection light reflected from the inspection area;

reflection means that reflects an incoming inspection light in a direction opposite to an incident direction;

optical path length adjustment means that causes the reflection means to move in an optical axis direction of the reference light; and detection means that detects, with the reflection means having been moved, an interference signal between the reference light and the light under inspection and acquires a reflection light intensity distribution, as well as acquiring spectral information from the light under inspection, and wherein the detection means further generates a three-dimensional tomographic image from the acquired reflection light intensity distribution, by the drive means causing the OCT to move, and outputs the generated three-dimensional tomographic image and the spectral information, as three-dimensional spectroscopic information.

[Supplementary Note 8]

The excrement analysis device according to supplementary note 7, further including optical transmission means that causes the inspection light and the light under inspection to transmit between the inspection area and the half mirror.

[Supplementary Note 9]

The excrement analysis device according to any one of supplementary notes 1 to 8, wherein the light source emits laser light, as the inspection light, toward an inspection area.

[Supplementary Note 10]

The excrement analysis device according to any one of supplementary notes 1 to 9, wherein the analysis means includes:
space extraction means that extracts a first space containing the largest amount of urine components and a second space containing the largest amount of fecal components from the spectroscopic information that has been output; and
component analysis means that outputs a result of analysis of urine and feces on the basis of spectral information regarding the extracted first space and second space.

[Supplementary Note 11]

The excrement analysis device according to supplementary note 10, wherein the component analysis means determines whether a specific component including any of sugar, protein, uric acid, sodium, potassium, stress hormone, and blood is contained in urine and feces and, if the specific component is contained, identifies the amount of the contained component, and outputs the amount as the result of analysis.

[Supplementary Note 12]

The excrement analysis device according to supplementary note 11, wherein the component analysis means outputs, as a result of analysis, a relative value of the identified amount.

[Supplementary Note 13]

The excrement analysis device according to any one of supplementary notes 10 to 12,
wherein the analysis means further includes storage means that stores the result of analysis, and
wherein the component analysis means updates the result of analysis stored in the storage means with a newly acquired result of analysis and outputs the updated result of analysis.

[Supplementary Note 14]

The excrement analysis device according to any one of supplementary notes 1 to 13, further comprising:
a collection container, which is a transparent container with an open top and which is embedded such that an open surface is exposed to the bowl's inner surface,
wherein the light source emits an inspection light toward an inspection area in the collection container.

[Supplementary Note 15]

The excrement analysis device according to any one of supplementary notes 1 to 14, wherein the spectroscopic information acquisition means outputs the spectroscopic information to the analysis means using wireless communication.

[Supplementary Note 16]

A toilet comprising:
a bowl into which urine and feces are discharged; and
the excrement analysis device according to any one of supplementary notes 1 to 15,
wherein the light source emits an inspection light toward an inspection area in the bowl.

[Supplementary Note 17]

A method for analyzing excrement, the method comprising:
receiving an inspection light emitted toward an inspection area in a toilet bowl, acquiring spectroscopic information from the received inspection light, and outputting the spectroscopic information;
extracting a first space containing the largest amount of urine components and a second space containing the largest amount of fecal components from the spectroscopic information that has been output; and
outputting a result of analysis of urine and feces on the basis of spectroscopic information regarding the extracted first space and second space.

INDUSTRIAL APPLICABILITY

The present invention can be applied to an ordinary toilet which is placed in an ordinary house, a public space, or the like and which is equipped with a bowl capable of holding a liquid in its inside.

The present application claims priority based on Japanese Patent Application No. 2014-216906 filed on Oct. 24, 2014, the entire disclosure of which is incorporated herein.

REFERENCE SIGNS LIST

10 Analysis device
20 Light source
30 Spectroscopic information acquisition means
40 Analysis means
100, 100C Analysis device
200 Collection container
300 Drive mechanism
400, 400B Spectroscopic information acquisition device
410 Light source
420 Half mirror
430 Reflection means
431 Optical path length adjustment means
440, 440B Spectroscopic information output means
441 Shutter
442, 442B Beam splitter
443, 443B Tomographic image detection means
444, 444B Spectral information detection means
500 Analysis device
510 Space extraction unit
520 Component analysis unit
600 Toilet
610 Bowl
700 Light source
800 Spectroscopic information acquisition device
900 Drive mechanism

The invention claimed is:

1. An excrement analysis device comprising:
a light source configured to emit an inspection light toward an inspection area in a toilet bowl;
a hyperspectral camera configured to receive the inspection light emitted toward the inspection area, acquire spectroscopic information from the received inspection light, and output the spectroscopic information;
a drive mechanism configured to cause the hyperspectral camera to move in an optical axis direction of the inspection light; and
a processor configured to extract a first space containing a largest amount of urine components and a second space containing a largest amount of fecal components from the spectroscopic information output by the hyperspectral camera, and output a result of analysis of urine and feces on the basis of spectroscopic information regarding the extracted first space and second space,
wherein the hyperspectral camera is configured to output three-dimensional spectroscopic information by moving in the optical axis direction.

2. The excrement analysis device according to claim 1, wherein the hyperspectral camera is configured to receive the inspection light reflected from the inspection area.

3. The excrement analysis device according to claim 1, wherein the processor is configured to determine whether a component including at least one of sugar, protein, uric acid, sodium, potassium, stress hormone, or blood is contained in urine and feces and, if the component is contained, identify the amount of the contained component, and output the amount as the result of analysis.

4. The excrement analysis device according to claim 1, further comprising:
a collection container, which is a transparent container with an open top and which is embedded such that an open surface is exposed to an inner surface of the collection container,
wherein the light source emits an inspection light toward an inspection area in the collection container.

5. A toilet comprising:
a bowl into which urine and feces are discharged; and
the excrement analysis device according to claim 1,
wherein the light source emits an inspection light toward an inspection area in the bowl.

6. An excrement analysis device comprising:
a light source configured to emit an inspection light;
a reflector configured to reflect an incoming inspection light in a direction opposite to an incident direction;
a half mirror configured to split the emitted inspection light into two inspection lights, output a first inspection light to the reflector and output a second inspection light to an inspection area in a toilet bowl, and output, as a reference light, the first inspection light reflected by the reflector and output, as a light under inspection, the second inspection light reflected from the inspection area;
an optical path length adjuster configured to cause the reflector to move in an optical axis direction of the reference light;
a processor configured to:
detect an interference signal between the reference light and the light under inspection;
acquire a reflection light intensity distribution and spectral information from the light under inspection;
generate a three-dimensional tomographic image from the acquired reflection light intensity distribution;
output the generated three-dimensional tomographic image and the spectral information, as three-dimensional spectroscopic information;
extract a first space containing a largest amount of urine components and a second space containing a largest amount of fecal components from the three-dimensional spectroscopic information; and
output a result of analysis of urine and feces on the basis of spectroscopic information regarding the extracted first space and second space.

* * * * *